United States Patent
Lee et al.

(10) Patent No.: US 9,255,060 B2
(45) Date of Patent: Feb. 9, 2016

(54) METHOD OF PREPARING AROMATIC CARBONATE FROM DIALKYL CARBONATE

(71) Applicant: Samsung SDI Co., Ltd., Yongin-si (KR)

(72) Inventors: Seung Hwan Lee, Uiwang-si (KR); Dong Baek Kim, Uiwang-si (KR); Jin Yong Bae, Uiwang-si (KR); Su Jeong Song, Uiwang-si (KR); Ju Hyun Lee, Uiwang-si (KR)

(73) Assignee: Samsung SDI Co., Ltd., Yongin-si (KR)

( * ) Notice: Subject to any disclaimer, the term of this patent is extended or adjusted under 35 U.S.C. 154(b) by 0 days.

(21) Appl. No.: 14/699,143

(22) Filed: Apr. 29, 2015

(65) Prior Publication Data

US 2015/0315122 A1 Nov. 5, 2015

(30) Foreign Application Priority Data

May 2, 2014 (KR) .......................... 10-2014-0053665

(51) Int. Cl.
*C07C 68/06* (2006.01)
*B01J 31/22* (2006.01)

(52) U.S. Cl.
CPC ............. *C07C 68/06* (2013.01); *B01J 31/2213* (2013.01); *B01J 2231/40* (2013.01); *B01J 2531/46* (2013.01); *B01J 2531/48* (2013.01)

(58) Field of Classification Search
None
See application file for complete search history.

(56) References Cited

PUBLICATIONS

Asao et al., Simultaneous Coordination and Double Activation Phenomena of Carbonyl and Epoxy Oxygens by Bis-Titanium Reagent as a Bidentate Lewis Acid Catalyst. Tetrahedron Letters, 1998, 39, 3729-3732.*

* cited by examiner

*Primary Examiner* — Michael Barker
*Assistant Examiner* — Po-Chih Chen
(74) *Attorney, Agent, or Firm* — Additon, Higgins & Pendleton, P.A.

(57) ABSTRACT

A method of preparing an aromatic carbonate includes reacting a dialkyl carbonate with an aromatic alcohol in the presence of a catalyst represented by Formula 1. With the method, aromatic carbonate can be prepared from a dialkyl carbonate in high yield using a catalyst capable of increasing initial reactivity of the dialkyl carbonate.

[Formula 1]

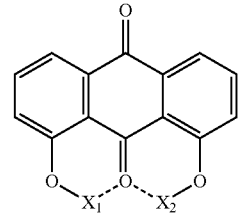

wherein $X_1$ and $X_2$ are the same or different and are each independently $M-(OR_1)_3$ or

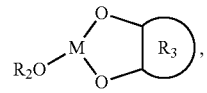

wherein M is a Group IV transition metal, $R_1$ and $R_2$ are the same or different and are each independently a substituted or unsubstituted $C_1$ to $C_{20}$ hydrocarbon group, and $R_3$ is a substituted or unsubstituted $C_5$ to $C_{20}$ cyclic alkylene group or arylene group.

8 Claims, No Drawings

METHOD OF PREPARING AROMATIC CARBONATE FROM DIALKYL CARBONATE

CROSS-REFERENCE TO RELATED APPLICATION

This application claims priority under 35 USC Section 119 to and the benefit of Korean Patent Application 10-2014-0053665, filed on May 2, 2014, the entire disclosure of which is incorporated herein by reference.

FIELD OF THE INVENTION

The present invention relates to a method of preparing an aromatic carbonate from a dialkyl carbonate.

BACKGROUND

An aromatic carbonate is an eco-friendly carbonyl source capable of replacing phosgene which is a deadly toxic compound. An aromatic carbonate may be obtained through reaction of an aromatic alcohol compound with carbon monoxide, carbon dioxide, or urea. However, this reaction is associated with problems such as generation of by-products, inflow of impurities into a product, use of expensive catalysts, complex processes, and the like.

To overcome these problems, there has been developed a method of preparing an aromatic carbonate through transesterification of an aliphatic carbonate (dialkyl carbonate) with an aromatic alcohol. Examples of catalysts used in transesterification may include PbO, $TiX_4$ (X being an alkoxy group, an aryloxy group, or halogen), $SnR_2(X)_2$ (R being an alkyl group, and X being an alkoxy group, an aryloxy group, or a halogen element).

However, despite high stability, a PbO catalyst has low activity, thereby causing very slow transesterification. Accordingly, unreacted dialkyl carbonate must be recycled many times. Thus, there is a need for a catalyst which exhibits increased reactivity to reduce such a recycling process. $TiX_4$ and $SnR_2(X)_2$ have disadvantages of lack of stability and generation of substantial amounts of by-products, such as ether, despite higher activity than PbO.

Therefore, there is a need for a method of stably preparing an aromatic carbonate in high yield using dialkyl carbonate as a starting material.

SUMMARY

Embodiments of the present invention provide a method of preparing an aromatic carbonate from a dialkyl carbonate and an aromatic alcohol in high yield using a catalyst capable of increasing initial reactivity of the dialkyl carbonate.

The method includes reacting a dialkyl carbonate with an aromatic alcohol in the presence of a catalyst represented by Formula 1:

[Formula 1]

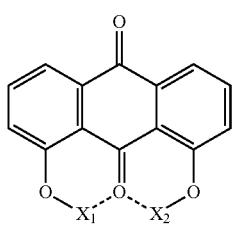

wherein $X_1$ and $X_2$ are the same or different and are each independently $M-(OR_1)_3$ or

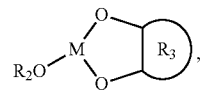

wherein M is a Group IV transition metal, $R_1$ and $R_2$ are the same or different and are each independently a substituted or unsubstituted $C_1$ to $C_{20}$ hydrocarbon group, and $R_3$ is a substituted or unsubstituted $C_5$ to $C_{20}$ cyclic alkylene group or substituted or unsubstituted $C_5$ to $C_{20}$ arylene group.

In one embodiment, the catalyst may include at least one of compounds represented by Formulas 1a, 1b and 1c:

[Formula 1a]

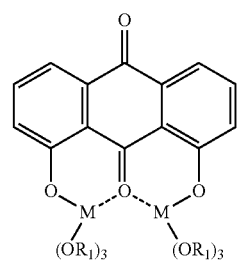

[Formula 1b]

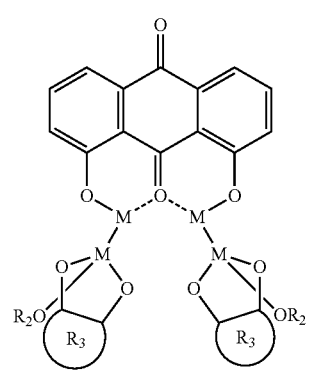

[Formula 1c]

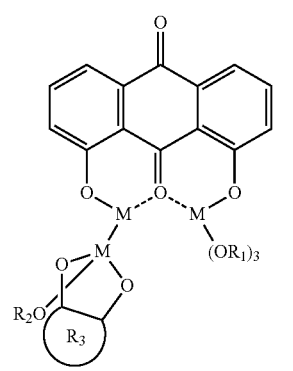

wherein M, $R_1$, $R_2$ and $R_3$ are the same as defined in Formula 1.

In exemplary embodiments, a dose of the catalyst may range from about 10 ppm to about 1,000 ppm based on the standard weight of the dialkyl carbonate.

In exemplary embodiments, the reacting a dialkyl carbonate with an aromatic alcohol may be performed at a temperature of about 100° C. to about 300° C.

In exemplary embodiments, the dialkyl carbonate may be represented by Formula 2:

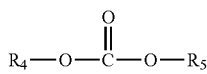
[Formula 2]

wherein $R_4$ and $R_5$ are the same or different and are each independently a $C_1$ to $C_6$ alkyl group.

In one embodiment, the aromatic alcohol may be represented by Formula 3:

 [Formula 3]

wherein Ar is a substituted or unsubstituted $C_6$ to $C_{20}$ aryl group.

DETAILED DESCRIPTION

Exemplary embodiments now will be described more fully hereinafter in the following detailed description, in which some, but not all embodiments of the invention are described. Indeed, this invention may be embodied in many different forms and should not be construed as limited to the embodiments set forth herein; rather, these embodiments are provided so that this disclosure will satisfy applicable legal requirements.

A method of preparing an aromatic carbonate according to the present invention includes reacting a dialkyl carbonate with an aromatic alcohol in the presence of a catalyst represented by Formula 1.

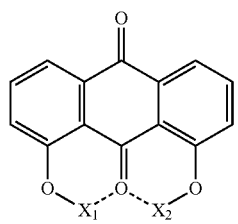
[Formula 1]

wherein $X_1$ and $X_2$ are the same or different and are each independently M—$(OR_1)_3$ or

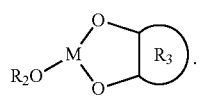

As used herein, M may be a Group IV transition metal, for example, titanium (Ti), zirconium (Zr), and/or hafnium (Hf), for example titanium (Ti). $R_1$ and $R_2$ may be the same or different and may each independently be a substituted or unsubstituted $C_1$ to $C_{20}$ hydrocarbon group, for example, a substituted or unsubstituted $C_1$ to $C_{20}$ alkyl group and/or a substituted or unsubstituted $C_6$ to $C_{20}$ aryl group, for example a substituted or unsubstituted $C_6$ to $C_{20}$ aryl group, such as a phenyl group. $R_3$ may be a substituted or unsubstituted $C_5$ to $C_{20}$ cyclic alkylene group and/or substituted or unsubstituted $C_5$ to $C_{20}$ arylene group, for example, a cyclohexylene group, a phenylene group, and the like.

As used herein, the term "substituted" means that a hydrogen atom is substituted with a substituent, such as a $C_1$ to $C_{10}$ alkyl group, a $C_6$ to $C_{12}$ aryl group, a halogen atom, and the like, and combinations thereof. In exemplary embodiments, the substituent may be a $C_1$ to $C_6$ alkyl group, for example a $C_1$ to $C_3$ alkyl group.

In addition, as used herein, the term "aromatic carbonate" includes alkylaryl carbonate, diaryl carbonate, and mixtures thereof.

The catalyst (Formula 1) of the present invention may be in the form of 1,8-dihydroxyanthraquinone coordinated with two Group IV transition metal compounds. Since the catalyst can activate one dialkyl carbonate by two transition metals coupled to an organic ligand, the catalyst can allow relatively rapid initial conversion as compared with typical catalysts containing a single transition metal.

In exemplary embodiments, the catalyst may be prepared by mixing a compound (1,8-dihydroxyanthraquinone) represented by Formula 4 with a transition metal compound represented by Formula 5a and/or Formula 5b, without being limited thereto.

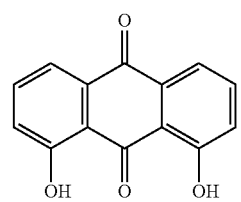
[Formula 4]

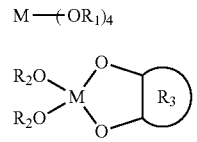
[Formula 5a]

[Formula 5b]

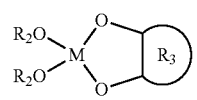

wherein M, $R_1$, $R_2$, and $R_3$ are the same as defined in Formula 1.

In preparation of the catalyst, an equivalence ratio of the compound represented by Formula 4 to the compound represented by Formula 5a and/or Formula 5b may range from 1:2 to 1:5, and mixing is performed by introducing the compound represented by Formula 4 and the compound represented by Formula 5a and/or Formula 5b into a solvent, such as dichloromethane, chloroform, and/or phenol at room temperature (about 25° C.) at atmospheric pressure (about 1 bar), without being limited thereto.

In exemplary embodiments, the catalyst may include at least one of compounds represented by Formulas 1a, 1b and/or 1c.

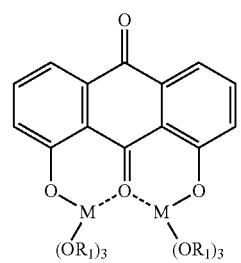
[Formula 1a]

[Formula 1b]

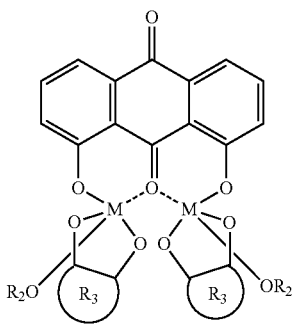

[Formula 1c]

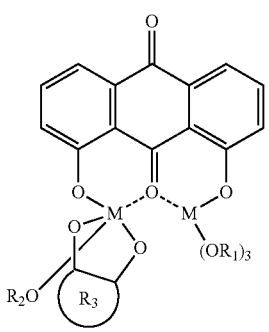

wherein M, $R_1$, $R_2$, and $R_3$ are the same as defined in Formula 1.

In exemplary embodiments, in reaction, a dose of the catalyst (in terms of metal) may range from about 10 ppm to about 1,000 ppm, for example, about 30 ppm to about 500 ppm, and as another example about 40 ppm to about 300 ppm, based on a weight of the dialkyl carbonate. Within this range, it is possible to increase initial reactivity of the dialkyl carbonate and to facilitate recovery of the catalyst after completion of reaction.

The dialkyl carbonate used in the present invention may be represented, for example, by Formula 2.

[Formula 2]

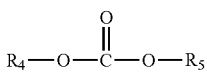

wherein $R_4$ and $R_5$ are the same or different and are each independently a $C_1$ to $C_6$ alkyl group.

In exemplary embodiments, examples of the dialkyl carbonate may include without limitation dimethyl carbonate, diethyl carbonate, dipropyl carbonate, dibutyl carbonate, methylethyl carbonate, methylpropyl carbonate, ethylpropyl carbonate, and the like, and combinations thereof. For example, the dialkyl carbonate may be dimethyl carbonate.

The aromatic alcohol (aromatic hydroxy compound) used in the present invention may be represented by Formula 3.

Ar—OH  [Formula 3]

wherein Ar is a substituted or unsubstituted $C_6$ to $C_{20}$ aryl group.

In exemplary embodiments, examples of the aromatic alcohol may include without limitation phenol, cresol (or an isomer thereof), xylenol (or an isomer thereof), trimethyl phenol (or an isomer thereof), tetramethyl phenol (or an isomer thereof), ethyl phenol (or an isomer thereof), propyl phenol (or an isomer thereof), butyl phenol (or an isomer thereof), diethyl phenol (or an isomer thereof), methylethyl phenol (or an isomer thereof), methylpropyl phenol (or an isomer thereof), dipropyl phenol (or an isomer thereof), methylbutyl phenol (or an isomer thereof), pentyl phenol (or an isomer thereof), hexyl phenol (or an isomer thereof), cyclohexyl phenol (or an isomer thereof), methoxy phenol (or an isomer thereof), ethoxy phenol (or an isomer thereof), naphthol (or an isomer thereof), various substituted naphthols, hydroxypyridine (or an isomer thereof), hydroxycoumarin (or an isomer thereof), hydroxyquinoline (or an isomer thereof), and the like, and combinations thereof. For example, the aromatic alcohol may be a $C_6$ to $C_{10}$ aromatic group-containing alcohol, for example phenol. An aromatic group of a prepared aromatic carbonate varies depending upon an aromatic alcohol used in preparation of the aromatic carbonate. For example, when phenol is used, it is possible to prepare alkylphenyl carbonate, diphenyl carbonate, and the like.

In exemplary embodiments, a mole ratio of the dialkyl carbonate to the aromatic alcohol (dialkyl carbonate:aromatic alcohol) may range from about 1:1 to about 1:10, for example, about 1:1.5 to about 1:5. Within this range, the aromatic carbonate can be obtained in high yield.

In the method of preparing an aromatic carbonate according to the present invention, reaction (transesterification) of the dialkyl carbonate with the aromatic alcohol is performed in the presence of the transesterification catalyst represented by Formula 1.

In one embodiment, the reaction may be performed at a temperature of about 100° C. to about 300° C., for example, about 150° C. to about 250° C., and as another example about 200° C. to about 230° C. and at a pressure of about 1 bar to about 30 bar, for example, atmospheric pressure (about 1 bar) to about 10 bar for about 1 second to about 180 minutes, for example, about 1 minute to about 20 minutes. Within this range, it is possible to secure rapid initial reaction, and thus to obtain the aromatic carbonate in high yield.

In addition, when the prepared aromatic carbonate includes alkylaryl carbonate, the method may further include disproportionating the alkylaryl carbonate to produce diaryl carbonate and dialkyl carbonate, which is a by-product. Such disproportionation can be easily carried out by those skilled in the art.

Hereinafter, the present invention will be described in more detail with reference to the following examples. However, it should be understood that these examples are provided for illustration only and are not to be construed in any way as limiting the present invention.

EXAMPLE 1

Preparation of Aromatic Carbonate

A tubular reactor with an inner volume of 80 ml is disposed in an oil bath capable of maintaining constant temperature, and then phenol (130 mmol), dimethyl carbonate (65 mmol), and 30 ppm (4 mg) of a catalyst represented by Formula 1d based on the weight of the dimethyl carbonate are introduced into the reactor, followed by replacing oxygen in the reactor with nitrogen, and the reactor is heated to 230° C. Next, the reactor is maintained at 230° C. for 5 minutes to form an aromatic carbonate, for example methylphenyl carbonate. The reactor is cooled to room temperature using a cooler, followed by measuring a yield of the prepared aromatic carbonate (a conversion rate of the dimethyl carbonate) through liquid chromatography. Results are shown in Table 1.

[Formula 1d]

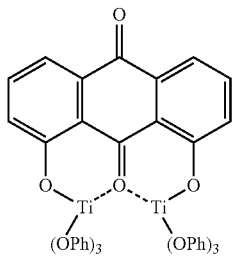

wherein Ph is a phenyl group.

EXAMPLES 2 to 4

Preparation of Aromatic Carbonate

An aromatic carbonate is prepared in the same manner as in Example 1, except that a dose (concentration) of the catalyst is changed as listed in Table 1. A yield of the prepared aromatic carbonate (a conversion rate of the dimethyl carbonate) is measured by liquid chromatography. Results are shown in Table 1.

EXAMPLE 5

Preparation of Aromatic Carbonate

An aromatic carbonate is prepared in the same manner as in Example 1, except that a catalyst represented by Formula 1e is used instead of the catalyst represented by Formula 1d. A yield of the prepared aromatic carbonate (a conversion rate of the dimethyl carbonate) is measured by liquid chromatography. Results are shown in Table 1.

[Formula 1e]

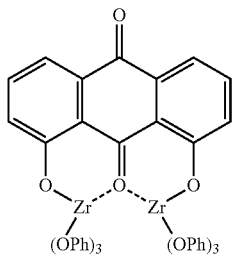

wherein Ph is a phenyl group.

COMPARATIVE EXAMPLES 1 to 4

Preparation of Aromatic Carbonate

An aromatic carbonate is prepared in the same manner as in Example 1, except that $Ti(Oph)_4$ is used as a catalyst instead of the catalyst represented by Formula 1d, and a dose (concentration) of the catalyst is changed as listed in Table 1. A yield of the prepared aromatic carbonate (a conversion rate of the dimethyl carbonate) is measured by liquid chromatography. Results are shown in Table 1.

COMPARATIVE EXAMPLE 5

Preparation of Aromatic Carbonate

An aromatic carbonate is prepared in the same manner as in Example 1, except that PbO is used as a catalyst instead of the catalyst represented by Formula 1d, and a dose (concentration) of the catalyst is changed as listed in Table 1. A yield of the prepared aromatic carbonate (a conversion rate of the dimethyl carbonate) is measured by liquid chromatography. Results are shown in Table 1.

Property Evaluation (1) Yield of aromatic carbonate (unit: %): A yield of an aromatic carbonate is calculated by Equation 1.

$$\text{Yield of aromatic carbonate (\%)} = (\text{mole number of prepared aromatic carbonate/mole number of introduced dialkyl carbonate}) \times 100 \quad \text{[Equation 1]}$$

TABLE 1

| | Catalyst | Dose of catalyst (ppm) | Reaction temperature (°C.) | Reaction time (min) | Yield of aromatic carbonate (%) |
|---|---|---|---|---|---|
| Example 1 | Formula 1d | 50 | 230 | 5 | 4.5 |
| Example 2 | Formula 1d | 100 | 230 | 5 | 5.3 |
| Example 3 | Formula 1d | 150 | 230 | 5 | 6.0 |
| Example 4 | Formula 1d | 200 | 230 | 5 | 6.3 |
| Example 5 | Formula 1e | 50 | 230 | 5 | 3.5 |
| Comparative Example 1 | $Ti(OBu)_4$ | 50 | 230 | 5 | 2.8 |
| Comparative Example 2 | $Ti(OBu)_4$ | 100 | 230 | 5 | 4.4 |
| Comparative Example 3 | $Ti(OBu)_4$ | 150 | 230 | 5 | 5.2 |
| Comparative Example 4 | $Ti(OBu)_4$ | 200 | 230 | 5 | 5.7 |
| Comparative Example 5 | PbO | 200 | 230 | 5 | 2.1 |

From the results shown in Table 1, it can be seen that, in preparation of an aromatic carbonate, use of a catalyst according to the invention (Examples 1 to 5) allows the aromatic carbonate to be prepared in relatively high yield as compared with typical catalysts (Comparative Examples 1 to 5), given that reaction temperature, reaction time, and catalyst concentration are the same. In particular, when the catalyst concentration is as low as 50 ppm (Example 1), the yield of the aromatic carbonate increased over 60% as compared with that in Comparative Example 1. Thus, it can be seen that, in Example 1, initial reaction proceeds very quickly. Here, the catalyst concentration in the Examples and Comparative Examples is expressed in terms of metal. Thus, it can easily be expected that, when the catalyst concentration is calculated based on the number of moles of catalyst, the yield of the aromatic carbonate of the Examples will be much higher than that of the Comparative Examples.

Many modifications and other embodiments of the invention will come to mind to one skilled in the art to which this invention pertains. Therefore, it is to be understood that the invention is not to be limited to the specific embodiments disclosed and that such modifications and other embodiments are intended to be included within the scope of the appended claims.

What is claimed is:

1. A method of preparing an aromatic carbonate, comprising: reacting a dialkyl carbonate with an aromatic alcohol in the presence of a catalyst represented by Formula 1:

[Formula 1]

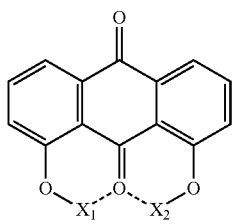

wherein $X_1$ and $X_2$ are the same or different and are each independently $M-(OR_1)_3$ or

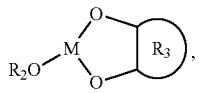

wherein M is a Group IV transition metal, $R_1$ and $R_2$ are the same or different and are each independently a substituted or unsubstituted $C_1$ to $C_{20}$ hydrocarbon group, and $R_3$ is a substituted or unsubstituted $C_5$ to $C_{20}$ cyclic alkylene group or substituted or unsubstituted $C_5$ to $C_{20}$ arylene group.

2. The method according to claim 1, wherein the catalyst comprises at least one of compounds represented by Formulas 1a, 1b and 1c:

[Formula 1a]

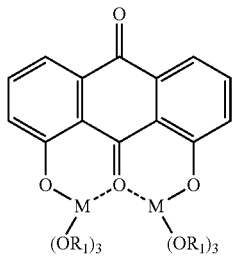

[Formula 1b]

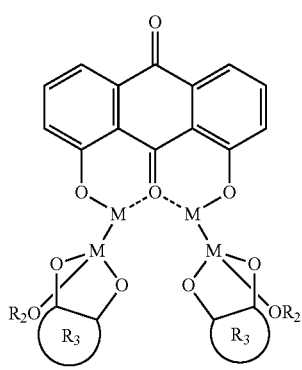

[Formula 1c]

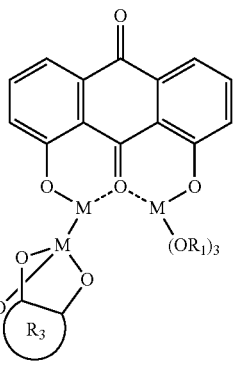

wherein M, $R_1$, $R_2$ and $R_3$ are the same as defined in Formula 1.

3. The method according to claim 1, wherein a dose of the catalyst ranges from about 10 ppm to about 1,000 ppm based on the weight of the dialkyl carbonate.

4. The method according to claim 1, wherein the reacting a dialkyl carbonate with an aromatic alcohol is performed at a temperature of about 100° C. to about 300° C.

5. The method according to claim 1, wherein the dialkyl carbonate is represented by Formula 2:

[Formula 2]

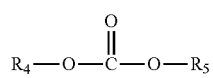

wherein $R_4$ and $R_5$ are the same or different and are each independently a $C_1$ to $C_6$ alkyl group.

6. The method according to claim 1, wherein the aromatic alcohol is represented by Formula 3:

   [Formula 3]

wherein Ar is a substituted or unsubstituted $C_6$ to $C_{20}$ aryl group.

7. The method according to claim 1, wherein the catalyst comprises a compound represented by Formula 1d:

[Formula 1d]

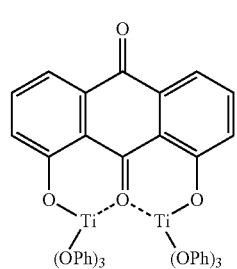

wherein Ph is a phenyl group.

8. The method according to claim 1, wherein the catalyst comprises a compound represented by Formula 1e:
[Formula 1e]
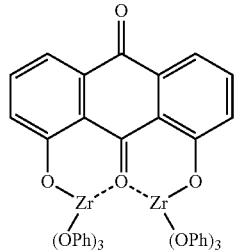
wherein Ph is a phenyl group.
* * * * *